United States Patent
Prystupa et al.

(10) Patent No.: US 12,379,296 B2
(45) Date of Patent: Aug. 5, 2025

(54) SPECTRAL DIAGNOSTIC SYSTEM

(71) Applicant: 12535441 Canada Ltd., Winnipeg (CA)

(72) Inventors: David Allan Prystupa, Pinawa (CA); John Stephen Pacak, Winnipeg (CA)

(73) Assignee: 12535441 Canada Ltd., Winnipeg (CA)

( * ) Notice: Subject to any disclaimer, the term of this patent is extended or adjusted under 35 U.S.C. 154(b) by 845 days.

(21) Appl. No.: 17/535,034

(22) Filed: Nov. 24, 2021

(65) Prior Publication Data

US 2022/0170839 A1 Jun. 2, 2022

Related U.S. Application Data

(60) Provisional application No. 63/118,713, filed on Nov. 26, 2020.

(51) Int. Cl.
*G01N 15/06* (2024.01)
*C12Q 1/04* (2006.01)
(Continued)

(52) U.S. Cl.
CPC .............. *G01N 15/06* (2013.01); *C12Q 1/04* (2013.01); *G01N 33/5008* (2013.01);
(Continued)

(58) Field of Classification Search
CPC ........... G01N 15/1459; G01N 15/1434; G01N 15/1433; G01N 15/147; G01N 15/1429;
(Continued)

(56) References Cited

U.S. PATENT DOCUMENTS 10,551,295 B2 * 2/2020 Bassler .................. G01N 21/64
2005/0249285 A1 * 11/2005 Chen .................... H04N 19/132
375/E7.254

(Continued)

FOREIGN PATENT DOCUMENTS

| EP | 0784201 | 7/1997 |
| EP | 2836958 | 2/2015 |
| WO | WO2009152437 | 12/2009 |

*Primary Examiner* — Shogo Sasaki (74) *Attorney, Agent, or Firm* — Adrian D. Battison; Ade & Company Inc.; Ryan W. Dupuis (57) ABSTRACT

A biological sample is analyzed for presence of a causing agent such as a virus, bacteria or cancer which generates a series of different states in the sample. The sample is separated into sub-samples where at least some of the sub-samples include portions of the sample at different states. Electromagnetic radiation interacts with the samples to obtain a spectrum of sub-sample properties which is compared with a plurality of reference spectra obtained from testing a plurality of sub-samples in respective ones of the different states to calculate a population distribution of the states of the sub-samples to obtain information about the causing agent. The population distribution can be analyzed at a single time or temporally over time to generate data relating to an effect of the causing agent. The population distribution is compared with a plurality of reference population distributions to generate data identifying the causing agent.

26 Claims, 1 Drawing Sheet

(51) Int. Cl.
   *G01N 33/50*      (2006.01)
   *G16H 10/40*      (2018.01)
   *G16H 50/20*      (2018.01)
   *G01N 15/075*     (2024.01)

(52) U.S. Cl.
   CPC ............. *G16H 10/40* (2018.01); *G16H 50/20*
                    (2018.01); *G01N 15/075* (2024.01)

(58) Field of Classification Search
   CPC .. G01N 33/5008; G01N 15/06; G01N 15/075;
                    G01N 2015/1006; C12Q 1/04; G16H
                    50/20; G16H 10/40
   See application file for complete search history.

(56)                References Cited

U.S. PATENT DOCUMENTS

2015/0066377 A1*  3/2015  Parchen ............ G06F 18/24155
                                                       702/19
2018/0172575 A1*  6/2018  Bassler .................. G01N 21/64

\* cited by examiner

SPECTRAL DIAGNOSTIC SYSTEM

This application claims the benefit under 35 USC 103 (e) from Provisional Application 63/118,713 filed Nov. 26, 2020.

This invention relates to a method for analyzing biological samples to obtain diagnostic information. More particularly the invention relates to a method for identifying a causing agent, such as a virus, bacteria or other agent such as cancer, of changes over time in a biological sample containing cells where the changes generate a series of different states in the biological sample.

RELATED APPLICATIONS

This disclosure is related to Multiple Pass Imaging Spectroscopy; U.S. Pat. No. 8,345,254 issued Jan. 1, 2013 by the present inventors hereafter referred to as the MPIS patent.

This disclosure is related to High Efficiency Multiplexing; U.S. Pat. No. 10,585,044 issued Mar. 10, 2020 by the present inventors hereafter referred to as the HEMS patent.

This disclosure is related to Magnetic Platform for Sample Orientation, U.S. provisional 62/978,675 filed Feb. 19, 2020 by the present inventors, hereafter the referred to as the MG patent and now published on 26 Aug. 2021 as WO 2012/163798.

This disclosure is related to Field Programmable Fluid Array; U.S. provisional 62/978,680 filed Feb. 19, 2020 by the current inventors and hereafter referred to as the FPFA patent and now published on 26 Aug. 2021 as WO 2012/163799.

This disclosure is related to Multi-dimensional Spectroscopy; U.S. provisional 63/059,298 filed Jul. 31, 2020 by the current inventors and hereafter referred to as the MDS patent and now filed on Jul. 28, 2021 as PCT/CA2021/051057.

This disclosure is related to Amplified Multiplex Absorption Spectroscopy; U.S. provisional Application 63/120,318 filed December 2020 by the present inventors, hereafter referred to as the AMAS patent.

This disclosure is related to Prystupa et al. (1993) Macromolecules 26, 1947-1955.

The disclosures of each of the above cited applications and published documents are incorporated herein by reference.

SUMMARY OF THE INVENTION

According to the invention there is provided a method for investigating a causing agent in a biological sample where the causing agent generates a series of different states in the biological sample, the method comprising the steps of:
  separating the biological sample into a plurality of sub-samples where at least some of the sub-samples include portions of the biological sample at different ones of said states;
  testing at least some of the sub-samples by interaction with electromagnetic radiation to obtain a spectrum of sub-sample properties;
  and carrying out a comparison of the spectrum from each sub-sample with a plurality of reference spectra obtained from testing a plurality of sub-samples in respective ones of the different states;
  using the comparisons to calculate a population distribution of the states of the sub-samples;
  and analyzing said population distribution to obtain information about the causing agent.

The term causing agent is intended to be a generic expression for any agent which affects the biological material. This can be an infectious agent such as a bacteria or virus. It can relate to diseases such as cancer or autoimmune disease. It can be another effect which generates the changes such as genetic defects or genetic changes including cancer. It can include aging which again generates changes in biological material over time. It can include other agents which affect the material such as pharmaceuticals, poisons or environmental pollutants.

In some cases, typically where the agent is known and information about its effect are required, the population distribution obtained is analyzed over time as the distribution changes to generate data relating to an effect of the causing agent.

In other cases, typically where the agent is not known and it is required to identify it, the population distribution is compared with a plurality of reference population distributions obtained from testing known samples to generate data identifying the causing agent The spectrum of the sub-sample properties can be obtained by: directing probe electromagnetic radiation into the sub-samples to interact with said sub-samples; collecting separately electromagnetic radiation transmitted, reflected, scattered or emitted from each sub-sample tested; and measuring an amplitude of the collected electromagnetic radiation at a plurality of measured wavelengths to obtain a measured spectrum from each sub-sample.

However other modalities can be used such as magnetic resonance or mass spectroscopy.

Preferably population distribution is compared with a plurality of reference population distributions obtained from testing known samples to generate data identifying the causing agent.

In one example the causing agent is a pharmaceutical which generates the changes in state.

That is one key feature is that the causing agent is identified by the population distribution in the sub-samples of different spectra indicative of different states of the biological sample in the different sub-samples. This method therefore relies on the changes that occur as the disease progresses rather than by attempting to directly identify the agent from its spectrum.

The causing agent is typically an infectious agent such as a bacteria or virus. However the causing agent can be a disease such as cancer all of which generate changes in state in the biological sample.

Where the causing agent is an infectious agent, this can be identified to the level of genus, species, or strain.

In an important feature which also can be used independently of the method defined above, the comparison of the measured spectrum from each sub-sample with a plurality of reference spectra is carried out by assigning one or more probabilities that the measured spectrum matches each reference spectrum, where the probability is determined based on spectral similarity between the measured spectrum and the reference spectrum, and the population distribution of the states of the sub-samples is calculated using the probabilities. That is there is no requirement to actually identify the sub-sample states from the spectra comparisons but only to generate a probability that it is one or another state. Based on a calculation of these probabilities, an actual population distribution can be calculated. Based on the above method, the population distribution can be compared with other known distributions to identify the causing agent. However the population distribution so determined can be used in other methods.

In one embodiment, at least one reference sub-sample state is associated with presence of an infectious agent proximate to or within a eukaryotic cell so as to interact with said eukaryotic cell and at least one reference sub sample state and at least one reference sub-sample state is associated with presence of a eukaryotic cell unaffected by interaction with an infectious agent. The interaction between an infectious agent and cell may be direct (primary) or secondary (mediated by the presence of at least one molecular species released by the infectious agent or released by another cell due to interaction with the infectious agent.

In one embodiment, at least one of the reference sub-sample states is associated with an environmental condition of the sample, such as pH, temperature thermal history and ionic concentrations.

In one embodiment, at least one of the reference sub-sample states is associated with a life cycle phase.

In one embodiment, at least one of the reference sub-sample states is further linked with at least one property of the reference sub-sample in an external database where the property depends on prior information about the source of the biological sample such as a medical record or part thereof relating to age, sex and underlying conditions, and genomic factors or a genomic sequence or part thereof.

In one embodiment, the causing agent is identified at least in part based on at least one property derived from sub-sample spectra probabilistically linked with a eukaryotic cell reference sub-sample state.

In one embodiment, the causing agent is identified at least in part based on a property from an external database associated with at least one reference sub-sample state probabilistically linked with a sub-sample.

In one embodiment, the causing agent is identified at least in part based on a spectral feature of at least one sub-sample that does not contain said infectious agent.

In one embodiment, the biological sample contains a plurality of different infectious agent types and a plurality of infectious agent types are identified to the level of genus, species or strain.

In one embodiment, at least one sub-sample spectrum is measured using an optical amplification device.

In one embodiment, at least one sub-sample is subjected to a sequence of different perturbations and for each perturbation a spectrum is measured so that at least one spectrum of said perturbed sub-sample is different from the spectrum of said sub-sample measured without perturbation whereby to provide additional spectra for the calculation of the population distribution. The perturbation can be caused singly or in combination by a change in temperature, a change in pressure, application of an electric field, application of a magnetic field, a change in solvent composition, a change in pH, or a change in ionic concentration. The sequence of perturbations applied to a sub-sample can depend at least in part on the spectrum of the sub-sample without perturbation.

In one embodiment, a stage of advancement of the causing agent is obtained by analysis of the distribution of sub-sample states, again by a comparison with known distributions from known stages of the causing agent.

In one embodiment, a cell is classified as normal or abnormal based at least in part on comparing multi-dimensional spectra of the cell with a database of reference multi-dimensional spectra.

In one embodiment, multidimensional spectra from at least one cell classified as normal is compared with a database of reference multi-dimensional spectra and a disease condition is diagnosed based at least in part on said comparison.

In one embodiment, the sub-samples are formed by dividing the sample by a partitioning system operable to separate the biological sample into a plurality of sub-samples wherein each sub-sample contains a volume element extracted from the biological sample and at least one volume element has a different composition than an average composition of the biological sample.

In one embodiment, a retroactive analysis is carried out of prior data based on identification and characterization of new infectious agent type.

In accordance with an important feature of the invention, the samples are divided by a partitioning system operable to separate the biological sample into a plurality of sub-samples wherein each sub-sample contains a volume element extracted from the biological sample that has a different composition than the average composition of the biological sample.

This can be done in a first method by using a flow cytometer or variant thereof. The flow cytometer is discussed in the above cited MPIS patent. A flow cytometer may be made massively parallel with the FPFA disclosure (with added sensors). In a second method a collection of cells is spread out on a surface and an optical sensor measures cell positions. Cells are selected for measurement (randomly or based on criteria such as size, shape, etc. A magnetic object is steered to the position of the selected cell, attaches to or encloses the selected cell, and translates the selected cell to a spectral measurement location. The cells to be measured may be selected to give a statistically significant number of each type. For example, 100 of type A, 100 of type B etc. In a third method, the sub-volumes are selected logically as regions within a larger volume.

The partitioning system may for example be the arrangement described in the above cited MPIS patent.

Briefly as one example, a fluid stream is divided into droplets and each droplet containing a biological sub-sample is individually directed to a different location on a substrate by for example an ink jet printer. Droplets lacking biological content may be discarded. This can be done in the flow cytometer where the droplet may have a small electric charge and be displaced by an electric field.

In accordance with an important optional feature of the invention which can be used independently with any of the above or following features, there is provided a sample placement system operable to place each biological sub-sample into a defined sample area occupied exclusively by the sub-sample. The sample placement system may for example be a plotter.

The partitioning system may for example be a fluidic network wherein different sub-samples are directed along different channels. Alternately the fluidic network may include a constriction that passes one sub-sample at a time. The fluidic network may be the arrangement described in the above cited FPFA patent.

The partitioning system may for example include a computation device that receives a sample image and partitions the sample image into sub-sample regions. The sub-sample regions may be pixels or contiguous blocks of pixels. The sub-sample regions may be selected based on a spectral property. For example, pixel regions may be selected from an image recorded with a confocal microscope based on the presence (or absence) of fluorescent emission detected in contiguous groups of pixels. The sub-sample regions may for example be selected from a spectral image recorded with an infrared microscope or a Raman microscope. The sub-sample regions may for example be selected from an amplified spectral image recorded using the arrangement of the above cited MPIS patent. The sub-sample regions may for example be selected from an amplified spectral image recorded using the arrangement of the above cited AMAS patent.

The partitioning system may for example be the arrangement described in the above cited MG patent wherein complex magnetic objects are manipulated with electromagnetic fields to individually select and orient biological sub-samples for analysis.

The biological samples may for example be fluids such as blood, saliva, urine, lymph, semen, faeces, etc. taken or extracted from a human or animal. The biological samples may for example be tissues or parts thereof taken or extracted from humans or animals or plants. The biological samples may for example be eukaryotic cells, bacteria, or virus particles associated with or extracted from a human or animal. The biological samples may for example be water samples taken from a water treatment plant or a water distribution system. A biological sample may for example contain a mixture of biological molecules in solution, aggregates of biological molecules, biological molecules organized as virus particles (viable or non-viable), and biological molecules organized as cells (viable or non-viable). The partitioning system may for example separate the biological sample into a plurality of sub-samples containing solution, a plurality of sub-samples containing aggregates, a plurality of sub-samples containing virus particles, and a plurality of sub-samples containing cells. Preferably each cell is contained in a different sub-sample.

For example, a sub-sample may be a large eukaryotic cell of mass $5 \times 10^{-7}$ g, possibly plus extra-cellular material excreted by the eukaryotic cell. For example, a sub-sample may be a prokaryote bacteria cell of mass the order of $4 \times 10^{-12}$ g, possibly plus extra-cellular material excreted by the prokaryotic cell.

For example, a sub-sample may be a viral particle of mass of the order of $1 \times 10^{-16}$ g. Preferably each virus particle not associated with a cell is contained in a different sub-sample. The purpose of using unitary sub-samples is to expose variability in the properties of biological units which provides a key advantage.

In accordance with an important feature of the invention, there is provided an arrangement to analyze electromagnetic radiation received from each defined sample volume. The arrangement to analyze may for example be a spectrometer. Preferably the spectrometer is of the type described in the above cited HEMS patent. The electromagnetic radiation received from each sample volume may be thermal emissions or emission following excitation (fluorescent emission). The electromagnetic radiation received from each sample volume may be scattered by molecules in the sample volume. The electromagnetic radiation received from each sample volume may be modified from incident electromagnetic radiation due to absorption by molecules in the sample volume. Probe electromagnetic radiation may be incident on a sample volume, interact with biological matter and interacted radiation is received for analysis.

In accordance with an important optional feature of the invention, there is provided a guidance system to generate and direct electromagnetic radiation into each defined sample volume and to extract electromagnetic radiation that has interacted with a sub-sample in each defined sample volume. The electromagnetic radiation may be x-rays with wavelength less than 10 nm. For example, x-rays may be used to measure atomic structure or meso-scale structure (SAXS). The electromagnetic radiation may be ultraviolet radiation with wavelengths between 10 nm and 450 nm or visible light with wavelengths between 450 nm and 700 nm. UV and visible radiation may for example be used to measure electronic transitions (absorbance), excite Raman spectra (including resonance Raman and CARS), excite fluorescent emission, and to probe structure via scattering. The electromagnetic radiation may be near infrared with wavelengths between 700 nm and 2500 nm, mid infrared with wavelengths between 2.5 microns and 25 microns, far infrared with wavelengths between 25 microns and 1000 microns, or microwave with wavelengths more than 1 mm. Radiation absorbed in these ranges may be used for example to identify molecular types present and their relative abundances within each defined sample volume. The defined sample volumes may be contiguous giving a spectral image or non-contiguous. The electromagnetic radiation may be collimated with angular divergence for example less than 10 mrad. The electromagnetic radiation may be focused to the dimensions of the defined sample volume. The electromagnetic radiation may be focused to a diffraction limited spot within the defined sample volume. The electromagnetic radiation interaction within a sub-diffraction limited volume within the defined sample volume may be enhanced via near field enhancement techniques as described in the above cited MG patent.

In accordance with an important feature of the invention, there is provided a database of reference spectra of biological sub-samples wherein each reference spectrum is linked with at least one physical attribute of the biological sub-sample. Preferably the database of reference spectra includes multi-dimensional spectra as described in the above cited MDS patent. The database of reference spectra may include spectra of biological molecules of a single type, spectra of a plurality of types of biological molecules with varying relative abundances, and spectra of complete biological units such as virus particles, prokaryotic cells and eukaryotic cells. The database may contain measured spectra, spectra generated from theoretical models, and combinations thereof. For example, the spectrum of water vapor generated from theory may have less noise than a measured spectrum of water vapor. The public HITRAN database contains the frequencies and relative intensities of most atmospheric gasses.

The spectrum of water vapor is a common interference in mid infrared spectra that may be removed by spectral subtraction. For example, reference spectra of biological macromolecules and aggregates thereof may be generated by lattice dynamics calculations. Preferably, each reference spectrum is linked with a plurality of physical attributes of the biological sub-sample. The physical attribute may be a genome sequence or part thereof. The physical attribute may be a genus, species or serotype designation established by a reference method. The physical attribute may be a disease symptom or sequence of symptoms. The physical attribute may be a probability or susceptibility to a disease symptom.

In accordance with an important feature of the invention, there is provided a database of reference sub-sample population distributions wherein at least one reference sub-sample distribution represents a distribution of sub-sample states known to be linked with an infectious agent. The infectious agent may be a known infectious agent or a novel infectious agent. The reference sub-sample distribution may for example include sub-samples corresponding with different stages of infection. The sub-samples may for example include normal (healthy) cells, cells altered by biological molecules generated by infectious agents or infected cells (secondary effect), cells directly infected by an infectious agent (primary effect), dead cells and fragments thereof, and infectious agents in isolation. Each enumerated type may be represented by several stages within the sub-sample distribution. For example, the spectra of cells in various stages of division are different. For example, the spectrum of a cell at a first stage of infection may differ from the spectrum of a cell at a later stage of infection.

In accordance with an important feature of the invention, there is provided a computation device. The computation device is any device operable to receive spectral data, perform the analysis described herein on the spectral data, and output results of the analysis. The computation device may include a plurality of logic processing units of different types, for example multiple CPU cores and FPGA units. The computation device may include a plurality of different machine-readable storage devices, for example volatile and non-volatile memory. The computation device may include a plurality of communication components that connect the computation device with I/O devices (keyboard, display, etc.) and with other computers via network connections. The computation device is operable to compare spectra of each biological sub-sample in the defined sample volume with a database of reference spectra. The computation device rather than provide an attempt at an exact match assigns one or more probabilities of match between each reference spectrum and spectrum of a biological sub-sample.

The computation device is then is operable to compare the population distributions of the sub-sample spectra types obtained from the above with a database of reference population distributions of sub-sample types.

In accordance with an important optional feature of the invention which can be used independently with any of the above or following features, there is provided a spectral imaging system operable to isolate spectral signals from each biological sub-sample. The spectral imaging system may for example be a Raman microscope. The spectral imaging system may for example be an infrared microscope. The spectral imaging system may for example be the arrangement described in the above cited MPIS patent. The spectral imaging system may for example be the arrangement described in the above cited AMAS patent.

In accordance with an important optional feature of the invention which can be used independently with any of the above or following features, there is provided a sample mapping system operable to assign spectral signals from spectral images to each biological sub-sample. The sample mapping system assigns each region of the image to one or more biological sub-samples and allocates the spectral amplitudes in the region to each biological sub-sample in said region. Preferably the image regions are selected as described in the above cited AMAS patent such that each image region contains either no biological sub-sample or one biological sub-sample.

In accordance with an important optional feature of the invention which can be used independently with any of the above or following features, there is provided an arrangement to apply perturbations to induce a plurality of different configurations of the biological sample in each defined sample volume. Different configurations of molecules within the biological sample may be induced by changing the temperature of the biological sample causing a change in molecular aggregation as described for example in above cited paper by Prystupa et al. Different configurations of molecules within the biological sample may be induced by changing the pH of the biological sample. Different configurations of molecules within the biological sample may be induced by adsorbing molecules onto a substrate and reorienting the substrate as described in the above cited MG patent. Different configurations of molecules within the biological sample may be induced by application of an electromagnetic or acoustic field within a sample volume as described in the above cited MDS patent. The electromagnetic field may be applied in the form of a laser pulse with sufficient instantaneous power to generate non-linear optical effects in the biological sample. The electromagnetic field may be applied as a DC field causing dipoles within the biological sample to align relative to the applied field. As discussed in the above cited MDS patent, an electromagnetic field oscillating at frequencies between 10 kHz and 10 MHz may be applied causing different populations of molecules or portions thereof within the biological sample to orient differently according to their respective moments of inertia, dipole moments, and interactions with neighboring molecules. The electromagnetic field may for example perturb quantum states of molecules within the biological sample via the Stark Effect or the Zeeman Effect.

In accordance with an important optional feature of the invention which can be used independently with any of the above or following features, there is provided an optical amplification system to increase the interaction of incident radiation with at least one sub-sample region. The optical amplification system may for example be the multi-pass device described in the above cited MPIS patent. The optical amplification system may for example be the multi-pass device described in the above cited AMAS patent. Amplification is achieved by passing a beam of electromagnetic radiation through sub-sample regions multiple times from different directions suffering absorption with each pass. The amplification is proportional to the number of times a ray in the beam passes through a sample region. Radiation incident on a detector array contains a convoluted image of the sample regions. The absorption of each sub-sample region is obtained by applying a deconvolution transformation.

In accordance with an important optional feature of the invention which can be used independently with any of the above or following features, when required, the population distribution is analyzed over time or temporally to generate data relating to an effect of the causing agent. That is, in some cases the infected cells may be in phase: that is the cells were infected at about the same time and have similar biochemical profiles. This is particularly effective when the infection or effect generated by the causing agent is simultaneous so that all affected cells are progressing through the different states simultaneously. In this case the additional information generated by the different measurements over time, or temporally, can provide an assistance in the analysis to determine the causing agent.

That is preferably, the sub-samples are held in an environmental chamber with defined environmental conditions for an incubation period and a plurality of measurements of each sub-sample are made at different times within the incubation period. That is the temporal evolution of each sub-sample in defined environmental conditions is measured to produce a multi-dimensional spectrum (amplitude, wavelength, time, environmental conditions and optionally additional perturbations such as applied electric field). The environmental conditions may for example include temperature, humidity, gas concentrations, nutrient concentrations, pH and ionic strength.

In an embodiment that may be used in combination with any of the preceding or following embodiments, spectra from sub-samples within a biological sample are classified by comparison with a database of reference sub-sample spectra.

The spectra of each sub-sample may be a temporal series of spectra and the database of reference sub-sample spectra for comparison may be a database of temporal series of spectra. That is the database of reference spectra contains spectra with the same dimensionality as the sub-sample spectra.

In some embodiments the classification is based at least in part on one or more non-spectral properties of the biological sample or the source thereof. The non-spectral properties include environmental factors such as temperature, thermal history, pH, ionic concentrations, and medical record parameters including age, sex and underlying medical conditions, and genomic factors. That is the set of records within a database of reference spectra utilized for comparison with a particular biological sample may depend on prior information about the source of the biological sample. The prior information in this case means prior to the particular analysis of the spectra data, rather than prior to collection of the spectra data. A spectral data set from a biological sample may be analyzed any number of times as more information about a non-spectral property becomes available.

In an embodiment that may be used in combination with any of the preceding or following embodiments, the database of reference spectra is extended to include sub-sample spectra from a biological sample and information associated with the biological sample. For example, in the case of a novel infectious agent, the sub-sample distribution of a first case may not correspond with any sub-sample distributions of known infectious agents within the reference database within the threshold for determination. The sub-sample distribution of the first case may be added to the database of reference spectra and used to identify other cases of the novel infectious agent both subsequently and retroactively by analyzing sub-sample distributions from prior measurements.

In an embodiment that may be used in combination with any of the preceding or following embodiments, spectra from sub-samples within a biological sample are classified by stage of development by comparison with a database of reference sub-sample spectra. The stage of development may for example be a stage in cell growth and division. The stage of development may for example be a stage of abnormal cellular function due to the influence of an infectious agent.

In an embodiment that may be used in combination with any of the preceding or following embodiments, an infectious agent is identified at least in part by the distribution of stages of development among sub-samples in a biological sample. For example, cells infected by a viral agent may pass through a sequence of states with different concentrations of biological molecules that may be distinguished by spectral measurements. For a large population of cells infected by a virus at different random times, the number of cells at each state in the sequence of states is proportional to the average time spent in that state relative to the time for all states in the sequence. The distribution of sub-sample states in this example hence represents a temporal profile that is unique to the infectious agent. The relative populations of abnormal cell states within a biological sample can represent a convolution of the temporal distribution of infection and the temporal sequence of abnormal cell states.

As stated above, in some cases the infected cells may be in phase: that is the cells were infected at about the same time and have similar biochemical profiles. In this case, the cells may be held in a controlled environment and measured a plurality of times in a temporal sequence to acquire spectra representative of a plurality of states. Each state is then weighted with the time spent in that state to produce a temporal distribution.

In an embodiment that may be used in combination with any of the preceding or following embodiments, spectra from sub-samples within a biological sample are classified by hierarchal clustering into a hierarchy with a plurality of levels and the cluster at each level of the hierarchy is further classified by comparison of spectra from the cluster with a database of reference spectra. For example, a hierarchal classification may first divide the sub-samples of a biological sample into groups comprising solution only, a cell, and an aggregate. Each group at the first level may be further classified. For example, the group of sub-samples containing a cell may be classified into subgroups containing a pro-karyotic cell, a eukaryotic cell, or both types. The classification may be repeated a plurality of times, for example until a sub-sample containing a cell is classified to the genus, species or strain level.

In an embodiment that may be used in combination with any of the preceding or following embodiments, an infectious agent is identified based on the presence of the number of sub-samples meeting a criterion exceeding a threshold value. For example, the criterion may be that the spectral similarity between a sub-sample spectrum and a reference sub-sample spectrum linked with an infectious agent is greater than a similarity threshold. The threshold number of sub-samples may for example be one. The threshold number of sub-samples may for example be a fraction of the total number of sub-samples extracted from a biological sample. The threshold number of sub-samples may be a fraction of sub-samples within a sub-population of sub-samples. For example, the sub-population may be the group of sub-samples on a common branch of a hierarchal classification.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

DETAILED DESCRIPTION

Embodiments of the present disclosure are described in detail with reference to the accompanying drawings. Detailed descriptions of constructions or processes known in the art may be omitted to avoid obscuring the subject matter of the present disclosure. Further in the following description of the present disclosure, various specific definitions found in the following description are provided to give a general understanding of the present disclosure, and it is apparent to those skilled in the art that the present disclosure can be implemented without such definitions.

Figure 1:
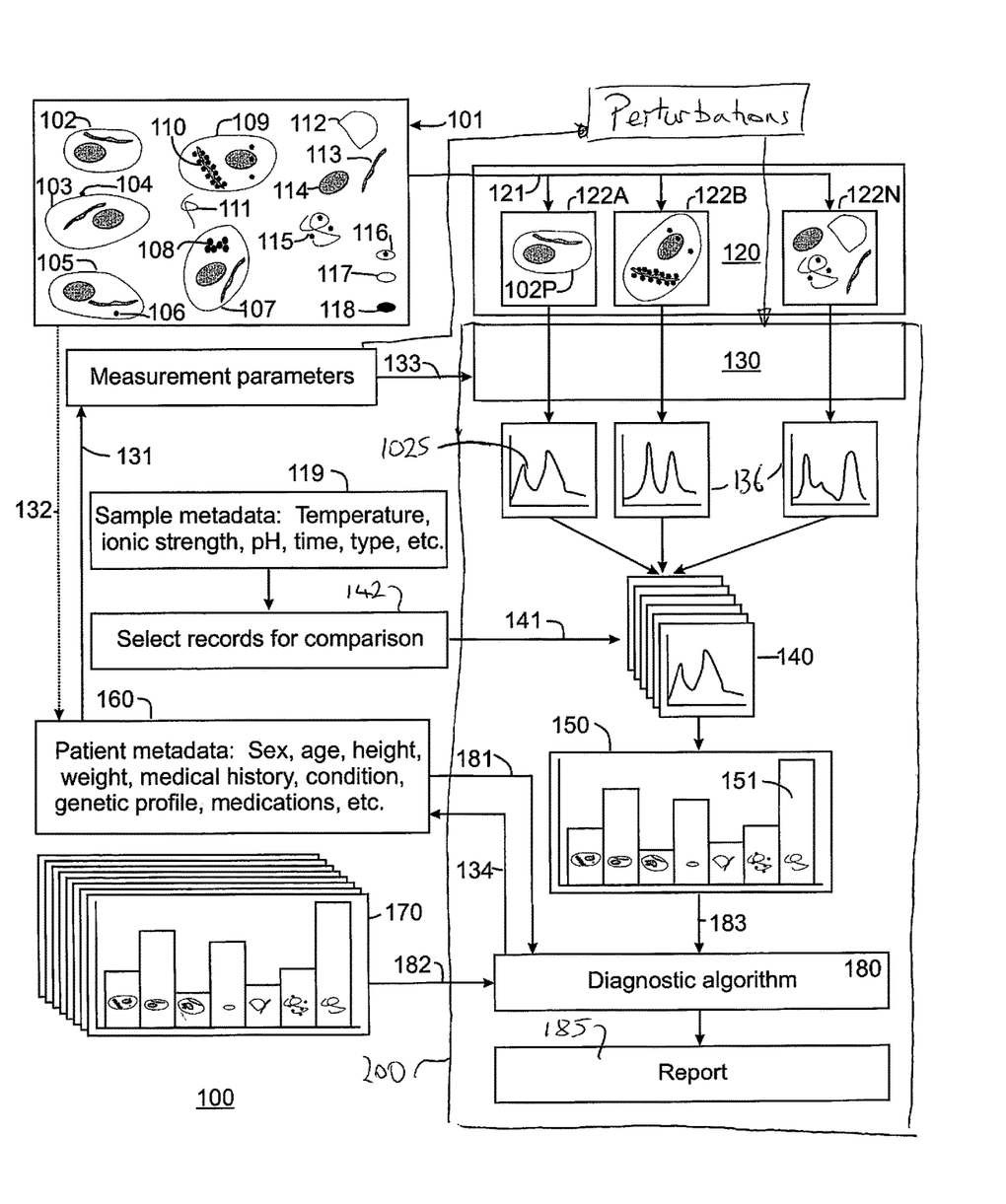
FIG. 1 shows a schematic illustration of a method according to the invention.

FIG. 1 shows a schematic of an embodiment of the invention generally indicated at 100. A biological sample for analysis 101 is obtained for example from a patient. Although this may be a human patient, the invention is not limited to human patients. The method of the invention may also be applied to veterinary patients and to plant disease and to water samples.

Biological sample 101 may contain uninfected eukaryotic cells as indicated at 102. The uninfected cells may be in a normal or healthy state or may be in an abnormal state. The uninfected abnormal state manifest in a first cell may for example be due to a second order effect wherein a disease affects a second cell and the second cell alters the environment of the first cell. The uninfected abnormal state manifest in a first cell may for example be due to a first order effect wherein disease affects a second cell and the second cell releases signaling molecules received by the first cell. The signaling molecule may for example cause the first cell to synthesize biological molecules related to cell defense.

Biological sample 101 may contain eukaryotic cells at various stages of infection by a virus. A cell at the initial stage of infection with virus particle 104 attached to the cell membrane is indicated at 103. A later stage of infection with a virus particle 106 in the cell cytoplasm is indicated at 105. As indicated at 107, a cluster of virus particles 108 may form in the cytoplasm. As indicated at 109, virus particles may be clustered in association with an organelle as shown at 110. The sample may contain extra-cellular bio-molecules 111 released into solution by secretion or by rupture of a cell. Ruptured cells may release cell fragments 112, organelles 113, cell nuclei 114 and bio-molecules with associated virus particles 115. The biological sample 101 may contain different types of prokaryotic cells 117 and 118 which may also be infected with a virus as shown at 116.

The biological sample 101 is transferred as indicated at 121 to partitioning system 120. The partitioning system 120 divides the biological sample 101 into N sub-samples as indicated by sub-sample volumes 122A, 122B to 122N. The sub-sample volumes are chosen such that the biochemical composition of a sub-sample volume differs from the average biochemical composition of the biological sample 101. That is the volumes are selected so that most sub sample volumes differ from the average biochemical composition.

Preferably the sub-sample volumes are approximately the volume of a cell as indicated at 102P, a cell of type 102 partitioned into sub-sample volume 122A. In this way the volumes will typically contain different states of the biological material as shown in the material 101.

The sub-sample volumes may be contiguous, for example as separate volume elements in a flow or as separate non-mixing volume elements on a substrate surface. The surface may for example be imaged with a microscope and sub-sample volume elements selected from the image by a feature extraction algorithm. The sub-sample volumes may be discrete, for example selected by a flow cytometer and placed with a printer as discussed in the above cited MPIS patent. Alternately, complex magnetic objects may be used to select position and orient sub-samples for measurement as described in the above cited MG patent.

A computation device 200 for analyzing the sub-samples 120 is provided which includes a number of components and operations as shown. This includes a measurement system 130, a recognition algorithm 140, a population distribution calculation component 150 and a diagnostic algorithm 180 providing a report 185.

The sub-samples are transferred to the measurement system 130. As indicated at 131, the computation device receives or retrieves meta-data 160 about the source of biological sample 101. The meta-data 160 may for example include information from medical records of a patient. The meta-data 160 may for example include genomic information about a patient. The computation device 200 determines measurement parameters to be applied to the measurement device 130 based at least in part on the meta-data 160. The measurement parameters may for example include ranges of wavelengths to measure, spectral resolution required, measurement time for a required signal-to-noise ratio, polarization of incident and measured radiation, sub-sample orientation(s). Measurement parameters are transmitted as indicated at 133 to the measurement system 130. In addition, the computation device generates a sequence of perturbations as indicated at 135 to apply to the sub-samples at the measurement device 130.

As shown at 134, the meta-data 160 may be appended to include information from a first analysis of spectral data from biological sample 101 carried out by the diagnostic algorithm 180 and based at least in part on the appended information. In this way a second set of measurement parameters is determined and passed to measurement system 130. As indicated at 132, patient meta-data 160 may be appended with information from a second measurement system. For example, the second measurement means may sequence DNA from the biological sample 101. The resulting genomic information may by used in combination with spectral information in diagnostic algorithm 180 to predict patient outcomes.

In the simplest embodiment, the measurement system 130 is a spectrometer that measures spectra of each sub-sample sequentially. In another embodiment, the measurement system is a conventional spectral imaging system that measures spectra of a plurality of sub-sample regions in parallel, for example with a focal plane array. In preferred embodiments, amplified spectral imaging methods as described in the above cited MPIS patent or the above cited AMAS patent are used to improve the sensitivity of spectral measurements. In preferred embodiments, spectral measurements are made with the arrangement described in the above cited HEMS patent to improve the signal-to-noise ratio. In a preferred embodiment, spectral measurements are made with the multi-dimensional spectroscopy arrangement described in the above cited MDS patent. In a most preferred embodiment, spectral measurements are made with the arrangements of the above cited AMAS and MDS patents in combination.

In some embodiments, the measurement system 130 is a confocal microscope. In some embodiments, the measurement system 130 is a dynamic light scattering apparatus. In some embodiments, the measurement system 130 is a diffractometer.

As shown at 136, spectra obtained by the measurement system 130 for each sub-sample are presented as electronic files to recognition algorithm 140. For example, the spectrum indicated at 102S is from sub-sample 102P of type 102 in biological sample 101. The recognition algorithm 140 uses as indicated at 141 meta-data stored in a data base 119 about the biological sample such as temperature, pH and nutrients present to select a set of records that correspond to those growth conditions which is selected by an algorithm 142. This step is desirable because the state of biological samples to be used in the comparison at the recognition algorithm 140 depends on the growth conditions as discussed in the above cited MPIS patent.

The method includes the following steps:
Obtain patient sample
Spatially isolate sub-samples
a flow cytometer deposits selected particles at selected locations as described in the above cited MPIS patent
Sub samples are separated temporally along a flow tube and each sub-sample is measured in sequence as the sub-sample passes a measurement location. The flow may be continuous or interrupted. The flow may for example be regulated by the arrangement described in the above cited FPFA patent.
Sub-samples may be separated as different regions in an image. In some embodiments, the sub-sample regions are identified by analysis of an image recorded with a first set of wavelengths and spectral measurements of the identified sub-sample regions are made with a second set of wavelengths. For example, the first set of wavelengths may be visible wavelengths and the second set of wavelengths may be infrared wavelengths. For example, the first set of wavelengths may be visible wavelengths and the second set of wavelengths may be wavelengths of Raman scattered radiation. For example, sub-sample regions may be identified by a first set of wavelengths that correspond with fluorescent emission and the sub-sample regions are measured with a second set of infrared wavelengths.
Generate spectral collection parameters
Obtain spectra of each sub-sample
Classify each sub-sample
Generate population statistics of sub-samples
Adequate spectral data
Generate patient profile
Compare patient profile
Example 1: Identification of bacterial infection
Example 2: Identification of viral infection
Example 3: Identification of abnormal tissue As indicated at 120, the method includes the step of separating the biological sample into a plurality of sub-samples where at least some of the sub-samples include portions of the biological sample at different ones of said states;

As indicated at 130, the method includes the steps of:
testing at least some of the sub-samples by:
directing probe electromagnetic radiation into the sub-samples to interact with said sub-samples;
collecting separately electromagnetic radiation transmitted, reflected, scattered or emitted from each sub-sample tested;
measuring an amplitude of the collected electromagnetic radiation at a plurality of measured wavelengths to obtain a measured spectrum from each sub-sample.

As indicated at 140, the method includes the step of carrying out a comparison of the measured spectrum from each sub-sample with a plurality of reference spectra 142 obtained from testing a plurality of sub-samples in respective ones of the different states.

As indicated at 150, the method includes the step of using the comparisons to calculate a population distribution 151 of the states of the sub-samples.

As indicated at 180, the method includes the step of comparing the population distribution from step 150 with a plurality of reference population distributions 170 obtained from testing known samples and provided to the algorithm 180 at step 182 to generate data indicating the infectious agent in the sample 101 to provide the report 185.

In the recognition algorithm 140, a comparison is made of the measured spectrum from each sub-sample with a plurality of reference spectra. Instead of trying to finally determine the identification of each sub-sample, the algorithm 140 operate by assigning one or more probabilities that the measured spectrum matches each reference spectrum, where the probability is determined based on spectral similarity between the measured spectrum and the reference spectrum. The final population distribution of the states of the sub-samples to be compared with the reference distributions 170 is calculated using these probabilities.

The above system for selecting the sub-samples at step 121 provides least one reference sub-sample state which is associated with presence of an infectious agent, at least one reference sub-sample state which is associated with presence of a eukaryotic cell unaffected by an infectious agent and at least one reference sub-sample state which is associated with presence of a eukaryotic cell affected by an infectious agent. The infectious agent is also identified at least in part based on a spectral feature of at least one sub-sample that does not contain the infectious agent.

As indicated at 133, at least one of the reference sub-sample states is associated with an environmental condition of the sample, such as pH, temperature thermal history and ionic concentrations and at least one of the reference sub-sample states is associated with a life cycle phase.

As indicated at 160, at least one of the reference sub-sample states is further linked with at least one property of the reference sub-sample in an external database where the property depends on prior information about the source of the biological sample such as a medical record or part thereof relating to age, sex and underlying conditions, and genomic factors or a genomic sequence or part thereof.

The biological sample 101 can contain a plurality of different infectious agent types and a plurality of infectious agent types are identified to the level of genus, species or strain.

As indicated at 135, the sub-samples are subjected to a sequence of different perturbations and for each perturbation a spectrum is measured so that at least one spectrum of said perturbed sub-sample is different from the spectrum of said sub-sample measured without perturbation whereby to provide additional spectra for the calculation of the population distribution.

The diagnostic algorithm 180 can also detect a stage of advancement of the causing agent by analysis of the distribution of sub-sample states by comparing with previously known distributions from the data base 170.

The diagnostic algorithm 180 can also be used to classify as normal or abnormal based at least in part on comparing multi-dimensional spectra of the cell with a database of reference multi-dimensional spectra.

The diagnostic algorithm 180 can also use multidimensional spectra from at least one cell classified as normal to be compared with a database of reference multi-dimensional spectra so that a disease condition is diagnosed based at least in part on said comparison.

In the step 121, the sub-samples are formed by dividing the sample 101 by a partitioning system operable to separate the biological sample into a plurality of sub-samples 122A etc wherein each sub-sample contains a volume element extracted from the biological sample and at least one volume element has a different composition than an average composition of the biological sample.

The diagnostic algorithm 180 can also be used to carry out a retroactive analysis of prior data based on identification and characterization of new infectious agent type.

The invention claimed is:

1. A method for obtaining identifying information about a causing agent in a biological sample where the causing agent generates a series of different states in the biological sample, the method comprising the steps of:

separating the biological sample into a plurality of sub-samples where at least some of the sub-samples include portions of the biological sample at different ones of said states;

testing at least some of the sub-samples by interaction with electromagnetic radiation to obtain for each tested sub-sample a spectrum of sub-sample properties;

carrying out a comparison of the spectrum from each tested sub-sample with a plurality of reference spectra obtained from testing a plurality of sub-samples in respective ones of the different states to assign a probability that each sub-sample belongs to each different state;

using the probabilities assigned to each sub-sample to calculate a population distribution of the states of the sub-samples;

and comparing said population distribution with a database of reference sub-sample population distributions to obtain said identifying information about the causing agent.

2. The method according to claim 1 wherein the causing agent is a pharmaceutical which generates said changes in state.

3. The method according to claim 1 wherein the causing agent is an infectious agent or a disease all of which generate said changes in state.

4. The method according to claim 1 wherein said infectious agent is identified to the level of genus, species, or strain.

5. The method according to claim 1 wherein at least one reference sub-sample state is associated with presence of an infectious agent, wherein at least one reference sub-sample state is associated with presence of a eukaryotic cell unaffected by an infectious agent and wherein at least one reference sub-sample state is associated with presence of a eukaryotic cell affected by an infectious agent.

6. The method according to claim 1 wherein at least one of the reference sub-sample states is associated with an environmental condition of the sample, such as pH, temperature thermal history and ionic concentrations.

7. The method according to claim 1 wherein at least one of the reference sub-sample states is associated with a life cycle phase of the cells.

8. The method according to claim 1 wherein at least one of the reference sub-sample states is further linked with at least one property of the reference sub-sample in an external database where the property depends on prior information about the source of the biological sample such as a medical record or part thereof relating to age, sex and underlying conditions, and genomic factors or a genomic sequence or part thereof.

9. The method according to claim 1 wherein the causing agent is identified at least in part based on at least one property derived from sub-sample spectra probabilistically linked with a eukaryotic cell reference sub-sample state.

10. The method according to claim 1 wherein the causing agent is identified at least in part based on a property from an external database associated with at least one reference sub-sample state probabilistically linked with a sub-sample.

11. The method according to claim 1 wherein the causing agent is identified at least in part based on a spectral feature of at least one sub-sample that does not contain said infectious agent.

12. The method according to claim 1 wherein the biological sample contains a plurality of different infectious agent types and a plurality of infectious agent types are identified to the level of genus, species or strain.

13. The method according to claim 1 wherein at least one sub-sample spectrum is measured using an optical amplification device.

14. The method according to claim 1 wherein at least one sub-sample spectrum is measured using a multiplex absorption device.

15. The method according to claim 1 wherein at least one sub-sample spectrum is measured using an amplified multiplex absorption device.

16. The method according to claim 1 wherein at least one sub-sample is subjected to a sequence of different perturbations and for each perturbation a spectrum is measured so that at least one spectrum of said perturbed sub-sample is different from the spectrum of said sub-sample measured without perturbation whereby to provide additional spectra for the calculation of the population distribution.

17. The method according to claim 16 wherein the perturbation is caused singly or in combination by a change in temperature, a change in pressure, application of an electric field, application of a magnetic field, application of an acoustic field, a change in solvent composition, a change in pH, or a change in ionic concentration.

18. The method according to claim 16 wherein the sequence of perturbations applied to a sub-sample depends at least in part on the spectrum of the sub-sample without perturbation.

19. The method according to claim 1 wherein a stage of advancement of the causing agent is obtained by analysis of the distribution of sub-sample states.

20. The method according to claim 1 wherein a cell is classified as normal or abnormal based at least in part on comparing multi-dimensional spectra of the cell with a database of reference multi-dimensional spectra.

21. The method according to claim 20 wherein multidimensional spectra from at least one cell classified as abnormal is compared with a database of reference multi-dimensional spectra and a disease condition is diagnosed based at least in part on said comparison.

22. The method according to claim 1 wherein the sub-samples are formed by dividing the sample by a partitioning system operable to separate the biological sample into a plurality of sub-samples wherein each sub-sample contains a volume element extracted from the biological sample and at least one volume element has a different composition than an average composition of the biological sample.

23. The method according to claim 1 wherein a retroactive analysis is carried out of prior data based on identification and characterization of new infectious agent type.

24. The method according to claim 1 wherein said population distribution is analyzed over time to generate data relating to an effect of the causing agent.

25. The method according to claim 24 wherein the sub-samples are held in an environmental chamber with defined environmental conditions for an incubation period and a plurality of measurements of each sub-sample are made at different times within the incubation period to produce a multi-dimensional spectrum.

26. The method according to claim 25 wherein measured a plurality of times in a temporal sequence to acquire spectra representative of a plurality of states where each state is then weighted with the time spent in that state to produce a temporal distribution.

\* \* \* \* \*